United States Patent [19]

Hartmann et al.

[11] 3,982,127
[45] Sept. 21, 1976

[54] METHOD AND APPARATUS FOR DISPLAYING THE INTERNAL STRUCTURE OF AN OBJECT

[75] Inventors: Werner Hartmann, Berkheim; Hans-Joachim Queisser; Gregor Markewitz, both of Stuttgart; Ulli Rettenmaier, Reichenbach; Gunter Sprater, Stuttgart; Rüdiger Kniep, Hilden, all of Germany

[73] Assignee: Max-Planck-Gesellschaft zur Forderung der Wissenschaften e.V., Goettingen, Germany

[22] Filed: July 14, 1975

[21] Appl. No.: 595,588

[30] Foreign Application Priority Data

July 17, 1974 Germany............................ 2434391
Mar. 19, 1975 Germany............................ 2512103
Jan. 31, 1975 Germany............................ 2503986

[52] U.S. Cl............................ 250/273; 178/DIG. 5; 250/276; 250/280; 250/368
[51] Int. Cl.² ................... G01N 21/34; G01N 23/00
[58] Field of Search .......... 250/273, 272, 276, 280, 250/213, 402, 459, 460, 363 R, 368; 178/DIG. 5

[56] References Cited

UNITED STATES PATENTS

| 3,058,021 | 10/1962 | Dunn | 178/DIG. 5 |
|---|---|---|---|
| 3,558,893 | 1/1971 | Ball | 250/460 |
| 3,622,786 | 11/1971 | Walker et al. | 250/363 |

Primary Examiner—Alfred E. Smith
Assistant Examiner—T. N. Grigsby
Attorney, Agent, or Firm—Hans Berman

[57] ABSTRACT

The pattern of X-rays produced by interaction of a beam of X-rays and a tested object is converted to an optical signal by a fine-grained zinc silicate screen which is viewed by a television camera through a magnifying optical system. The combination of a fine-grained luminescent screen of high resolving power with a camera having a photosensitive surface of much lower resolving power and high sensitivity provides real-time images of structural details not heretofore visualized except by photographic processes.

28 Claims, 4 Drawing Figures

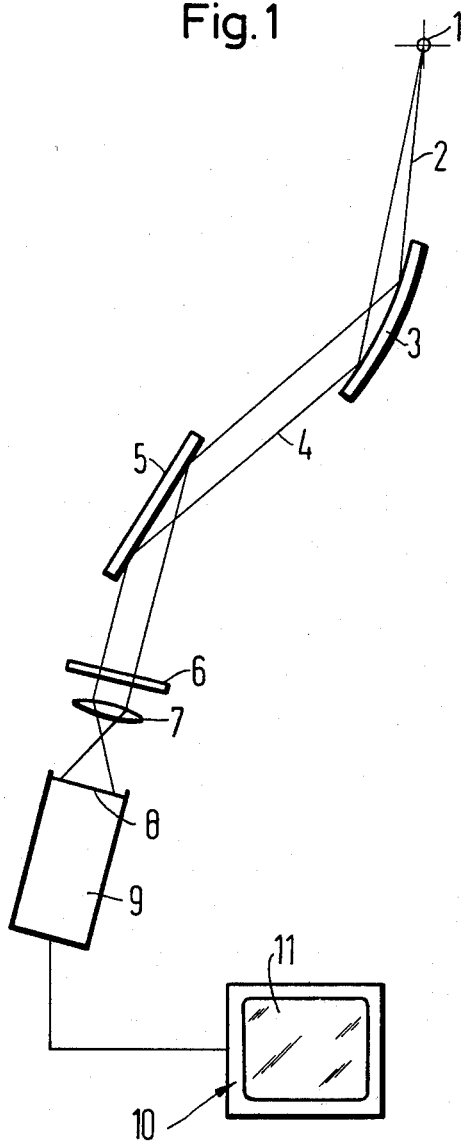
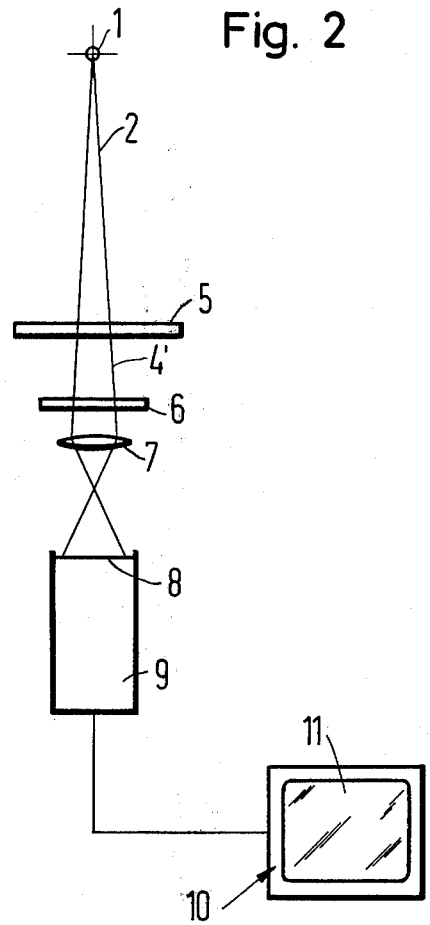

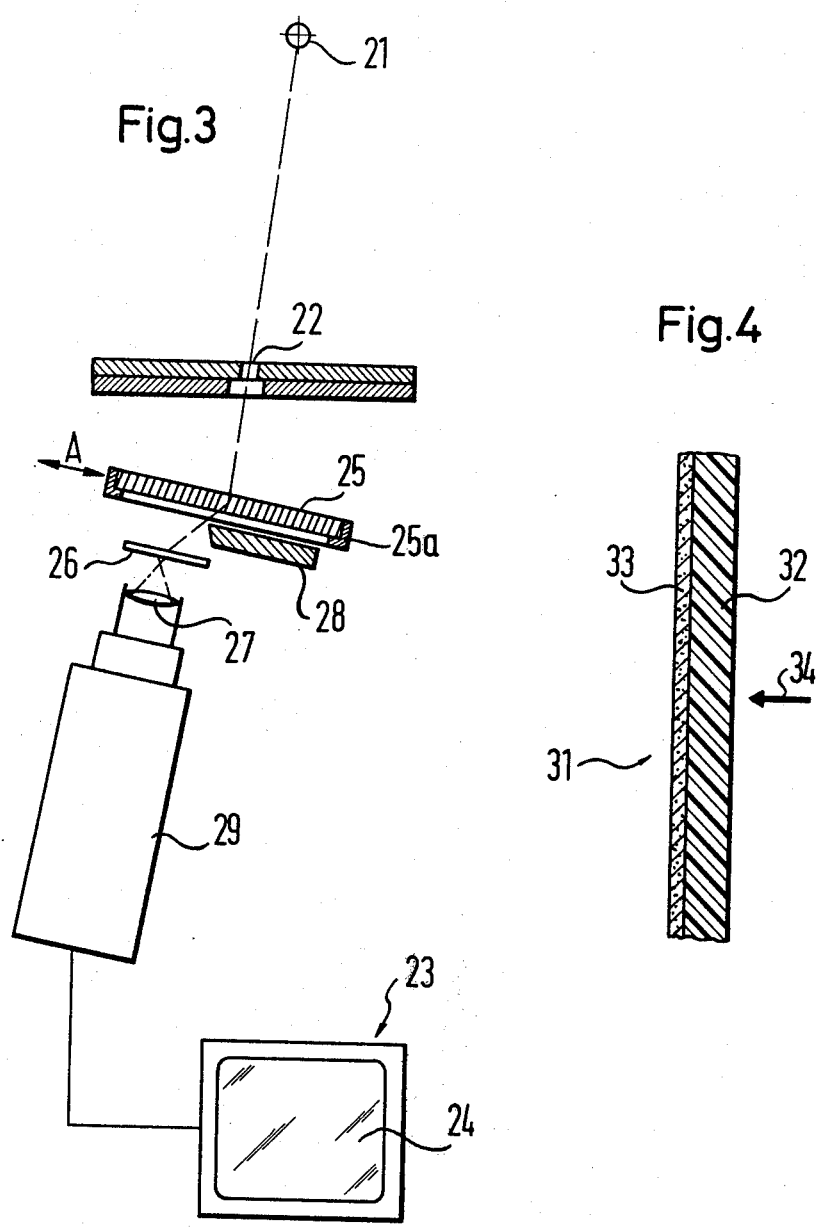

METHOD AND APPARATUS FOR DISPLAYING THE INTERNAL STRUCTURE OF AN OBJECT

This invention relates to direct display topography and fluoroscopy, and particularly to a method of displaying a visible image of the internal structure of an object by means of a beam of radiation, and to apparatus capable of performing the method.

In its more specific aspects, the invention relates to topography and fluoroscopy by means of a beam of X-rays and like radiation which passes through the tested object or is reflected or diffracted by the object.

Known systems of X-ray topography provide images of the fine structure of the tested object by two basic processes. In one known process, the radiation modified by interaction with the object is intercepted by a photographic emulsion which produces the desired visual image after processing. In the other process, the pattern of secondary radiation transmitted or emitted from the object is received by the photosensitive surface of a television camera and displayed on a monitor screen. The photographic process is capable of a resolution of 1 $\mu$m or 1000 lines per millimeter, but requires exposure times of approximately one hour to about 30 hours (see "Advances in X-Ray Analysis", vol. 10, 1967, pp. 1–8). Electronic display of the secondary beam pattern is available from a vidicon tube in which a charge density pattern is formed by photoconduction and stored on a photoconductor surface that is scanned by an electron beam (Applied Physics Letters, vol. 13, No. 11, Dec. 1, 1968, pages 387–389). While the electronic system instantaneously displays changes occurring in the tested object, the photosensitive surface cannot resolve details smaller than about 30 $\mu$m, such as are essential in crystal growth, formation and movement of dislocations. More recently, an electronic process achieving resolutions of slightly less than 25 $\mu$m has been disclosed, but still cannot approach the resolving power of the best photographic processes (Japanese J. of Applied Physics, vol. 11, No. 10, Oct. 1972, pages 1514–1521).

It is the primary object of this invention to provide a real-time display of the internal structure of a tested object at a resolution which comes closer to that available from the best photographic processes than the known electronic display systems.

According to a basic feature of this invention, the secondary beam of radiation generated by an object exposed to a suitable primary beam is intercepted by a luminescent screen of high resolving power which responds to the secondary beam by emitting a finely detailed visible image. This image is optically magnified and the magnified image is received by the photosensitive surface of a television camera to produce an electronically enlarged monitor image of the scanned photosensitive surface. Because of the intervening optical magnification, the relatively low resolving power of the photosensitive surface in the television camera is adequate to reproduce all detail capable of being resolved by the luminescent screen.

The invention is applicable to the non-destructive examination of objects by transmitted or reflected X-rays, but is suitable, in its basic aspects, to the investigation of materials by other high-energy radiation including ultraviolet light, gamma rays, and electron beams. It permits the instantaneous observation of changes in structures smaller than 10 $\mu$m.

The spacing between the tested object and the luminescent screen should be as small as possible for best resolving power and high sensitivity, and should preferably be no greater than is necessary to permit separation of the secondary beam of modified radiation from the portion of the primary beam which continues at an angle from the secondary beam after interaction with the tested object. The primary beam includes wavelengths or lines characteristic of the target material in the X-ray tube employed, principally of wavelengths $K\alpha_1$ and $K\alpha_2$, which produce divergent respective secondary rays. The screen must be close enough to the tested object that the divergence of these principal components of the secondary beam is too small to be resolved by the luminescent screen. The sensitivity of the process according to the invention is thus enhanced by the use of both components of the $K\alpha$ doublet without loss of resolution. It is further enhanced by the close spacing between the source of radiation and the examined object, and by the close spacing between the object and the luminescent screen.

The invention permits the direct observation of changes occurring in crystalline solids such as phase transformations, diffusion, thermal changes, and changes due to the implantation of ions, to elevated pressure, to magnetic fields, light, and other external factors. The formation of lattice defects and the growth of crystals are readily visualized. Processes in the manufacture of integrated circuits and other semi-conductor devices are capable of visual representation. Other applications will readily suggest themselves.

An essential element of this invention is the luminescent screen which produces a visible image in response to the secondary radiation emitted from the tested object. The known luminescent screens consist of a phosphor layer on a carrier sheet. The most widely employed phosphors consist essentially of zinc sulfide and a small amount of an activator which determines the color of the visible light generated in response to incident ionizing radiation. Glass and cardboard are the usual carrier materials, and their phosphor coated faces are directed toward the source of primary radiation. The known luminescent screens are not suitable for the purpose of this invention because their resolving power has a practical limit at about 25 $\mu$m. This is insufficient for visualizing small cracks or non-metallic inclusions in metallic structures and even less adequate for visualizing fine structure.

It has been found that the luminescence of zinc sulfide phosphors is reduced sharply when they are comminuted to a grain size smaller than about 25 $\mu$m, whereas zinc silicate ($Zn_2SiO_4$) can be ground to a particle size of much less than 5 $\mu$m without significant loss of luminosity, and that small amounts of manganese and rare earth metal compounds enhance the luminescent response of fine grains of zinc silicate phosphor to incident ionizing radiation. Resolutions of more than 500 lines per mm (less than 2 $\mu$m) are readily achieved.

The carriers employed for the purpose of the invention should be practically transparent to X-rays so that the phosphor-coated carrier surface may be directed toward the optical magnifying system and the photosensitive surface of the associated television camera. Suitable carriers include beryllium and plastic films or foils. Even these materials should not be used in sheets thicker than 100 $\mu$m, and a thickness of 6 $\mu$m or less is preferred for plastic foils. Among commercially avail-

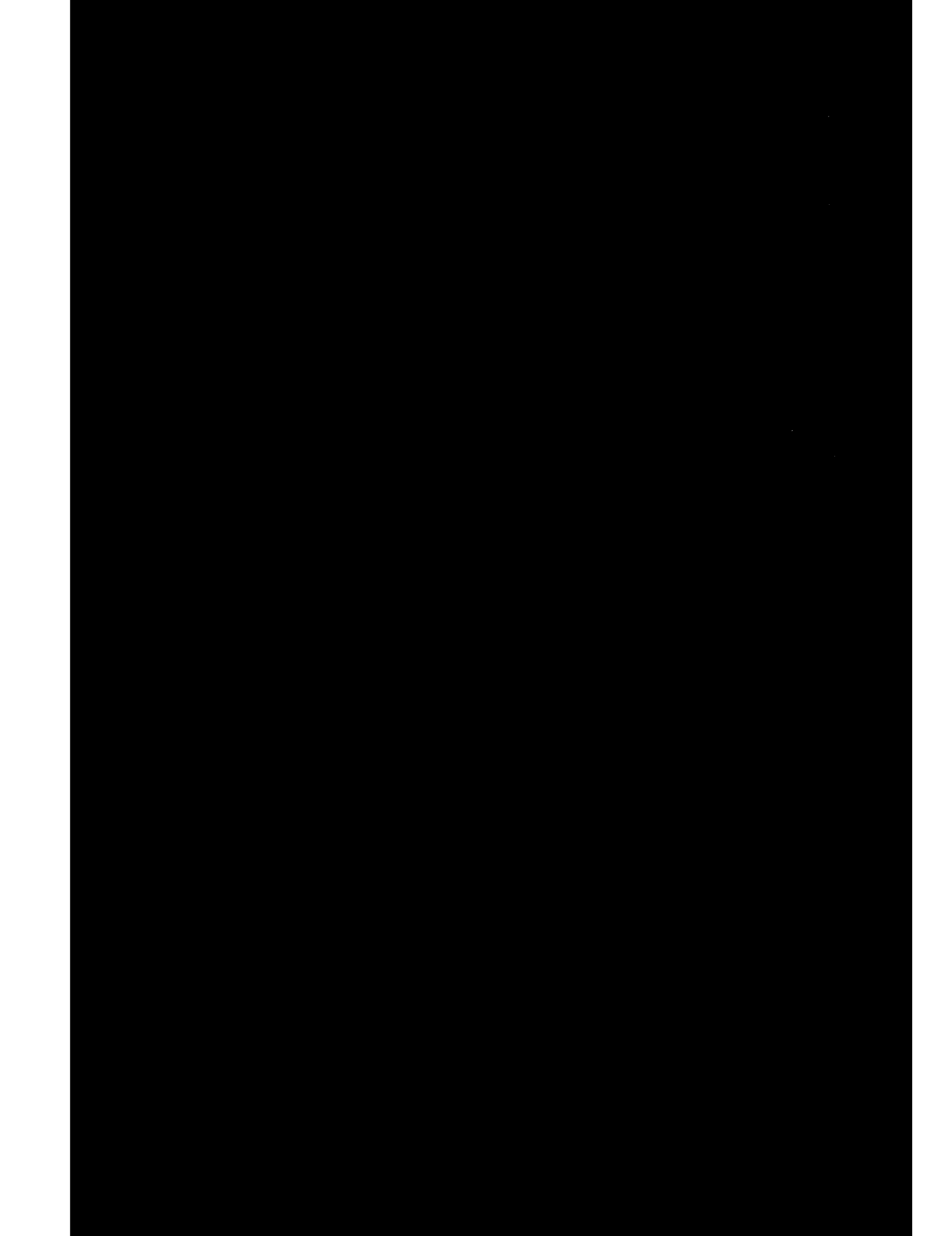

of a television camera 29. The further enlarged image can be viewed on the screen 24 of a television receiver 23.

For best results, the specimen to be investigated should be as close as possible to the source of X-rays 1, 21 and to the luminescent screen 6, 26. The close coupling of the specimen and the source of radiation improves the effective intensity of the X-rays. The actual distance is determined largely by structural features of the X-ray tube employed. It may be as small as 100 mm with some commercially available tubes (rotary anode tube RU 500 of Rigaku Denki, Tokyo, Japan). Best results are obtained when the primary beam of X-rays is emitted from the target face in the tube at an angle of 5° – 10°, preferably 8°. The maximum distance between the specimen and the screen 6, 26 is essentially determined by the resolving power of the luminescent screen. The principal characteristic lines of the diffracted radiation, that is, the $K_{\alpha_1}$ and $K_{\alpha_2}$ lines, diverge from the specimen and must be intercepted before they can produce separage images when their divergence exceeds the resolving power of the screen.

The distance of the lead shield 28 from the specimen in the direction of the primary beam should be as small as possible, but must be chosen completely to separate the residual primary beam from the secondary radiation. The point at which the two beams are separated must be spaced from the specimen at least a distance of $x$ mm which may be calculated from the equation $$x = \frac{W}{\tan \theta} + d$$

wherein $W$ is the transverse width of the primary beam in millimeters, $\theta$ is the Bragg angle defined by the primary beam and the diffracting lattice planes of the tested crystal, and $d$ is the thickness of the crystal in the direction of the primary beam in millimeters.

For best results, the distance of the lead shield 28 from the crystal 25 should not exceed 5 mm. For an X-ray tube having a molybdenum target, for a primary beam having a width of 0.4 mm, and for a silicon crystal 0.5 mm thick, the minimum distance $x$ calculated from the above formula for refraction from the 220 plane is 2.63 mm, and the two components of the $K_\alpha$ doublet diverge by less than 3 μm at this distance. The screen 26 should be as close to the shield 28 as possible, distances of less than 0.2 mm, preferably 0.05 – 0.1 mm, being both feasible and advantageous.

The stop 25 is preferably placed contiguously adjacent the window of the X-ray tube, and the specimen holder 25a is located no farther from the stop than is necessary to provide space for proper orientation of the selected lattice planes of the crystal 25 relative to the $K_\alpha$ radiation. The distance between the tested crystal 25 and the screen 26 should not be greater than 3 mm if the resolving power of the screen is better than 5 μm (200 lines per mm).

The linear magnification of the screen image achieved by the lens system 27 is preferably four or greater. The television camera is a vidicon employing a conventional EIC (electron induced conductivity) tube.

The apparatus shown in FIG. 3 and described above permits the display of a crystal section 0.5 mm × 2 mm at 60× total magnification within 1/25 second, that is the time required by the camera for scanning an image frame. In a crystal having almost 1000 dislocations per $cm^2$, all dislocations were visible. There were no double images.

As compared to known systems of X-ray topography, the apparatus shown in FIG. 3 enhances the intensity of the diffracted beam by the close spacing of the structural elements, and by the utilization of both the $K_{\alpha_1}$ and $K_{\alpha_2}$ lines. The image amplifying power of the television camera is fully utilized without impairing the reproduction of fine structure that is not visualized when the photosensitive surface of the camera directly receives the X-rays.

It should be understood, of course, that the foregoing disclosure relates only to preferred embodiments of the invention, and that it is intended to cover all changes and modifications of the examples of the invention herein chosen for the purpose of the disclosure which do not constitute departures from the spirit and scope of the invention set forth in the appended claims.

What is claimed is:

1. A method of displaying an image of the internal structure of an object which comprises:
   a. exposing said object to a primary beam of radiation sufficient to generate emission of a secondary beam of radiation from said object;
   b. intercepting said secondary beam by a luminescent screen responsive to said secondary beam to emit a visible image of said object;
   c. optically magnifying said image;
   d. receiving the magnified image on the photosensitive surface of a television camera;
   e. scanning said surface; and
   f. producing an electronically enlarged visual image of the image on said scanned surface,
      1. the resolving power of said screen being greater than the resolving power of said surface.

2. A method as set forth in claim 1, wherein said primary beam of radiation is a beam of X-rays, and said object is a crystal having a lattice plane and capable of diffracting a portion of said primary beam, said secondary beam consisting of the diffracted portion of said primary beam, and wherein the remainder of said primary beam passes in a straight line through said crystal and is separated from said secondary beam at a point spaced from said crystal, the spacing of said point from said crystal being at least $x$ mm, but not more than 5 mm, $x$ being defined by the equation $$x = \frac{W}{\tan \theta} + d$$

wherein $W$ is the transverse width of said primary beam in millimeters, $\theta$ is the Bragg angle defined by said primary beam and said plane, and $d$ is the thickness of said crystal in the direction of said primary beam in millimeters.

3. A method as set forth in claim 2, wherein said primary beam has characteristic components of wavelengths $K_{\alpha_1}$ and $K_{\alpha_2}$ respectively, said components producing divergent respective secondary rays, said spacing of said screen from said crystal being small enough to make the divergence of said secondary rays too small to be resolved by said screen.

4. A method as set forth in claim 3, wherein said primary beam is being separated from said seconary beam by being intercepted by a shield opaque to said X-rays.

5. A method as set forth in claim 3, wherein said primary beam is emitted from the metal target of an X-ray tube at an angle of 5° to 10° to the emitting face of said target.

6. A method as set forth in claim 3, wherein the power of resolution of said screen is at least 200 lines per millimeter.

7. A method as set forth in claim 6, wherein the spacing of said screen from said crystal is smaller than 3 millimeters.

8. A method as set forth in claim 7, wherein said screen consists essentially of a carrier and of a layer of zinc silicate on said carrier as a phosphor.

9. A method as set forth in claim 8, wherein said zinc silicate contains an amount of manganese sufficient to activate said phosphor.

10. A method as set forth in claim 7, wherein said television camera has a sensitivity of at least 150 microamperes per lumen.

11. A method as set forth in claim 3, wherein said primary beam is generated by refracting incident X-rays from an auxiliary crystal having an arcuate refracting surface.

12. A method as set forth in claim 11, wherein said auxiliary crystal consists of mica or quartz.

13. A method as set forth in claim 12, wherein the Bragg angle between said surface of said auxiliary cyrstal and said incident X-rays is 20°.

14. A method as set forth in claim 1, wherein the radiation of said primary beam is γ-radiation, ultraviolet radiation, or electron radiation.

15. Apparatus for displaying an image of the internal structure of an object which comprises:
   a. a source of a primary beam of radiation;
   b. object supporting means for supporting said object in a position in which the object is exposed to said primary beam for generating a secondary beam of modified radiation in response to said primary beam;
   c. a luminescent screen positioned for intersecting said modified radiation and capable of producing a visible image in response to the intersected radiation;
   d. a television camera having a photosensitive surface;
   e. optical means interposed between said screen and said surface for magnifying said visible image and for projecting the magnified image on said surface; and
   f. image producing means connected to said camera for electronically reproducing said magnified image, the resolving power of said screen being greater than the resolving power of said surface.

16. Apparatus as set forth in claim 15, wherein the linear magnification of said visible image by said optical means is approximately equal to the ratio of the resolving powers of said screen and of said surface respectively.

17. Apparatus as set forth in claim 15, further comprising shielding means interposed between said supporting means and said screen for shielding said screen form said primary beam without interfering with said secondary beam.

18. Apparatus as set forth in claim 15, wherein said source includes an X-ray generating tube and collimating means interposed between said tube and said object supported on said supporting means.

19. Apparatus as set forth in claim 18, wherein said screen is spaced not more than 3 millimeters from said object in said position.

20. Apparatus as set forth in claim 15, wherein the resolving power of said screen is at least 100 lines per millimeter.

21. Apparatus as set forth in claim 20, wherein said resolving power of the screen is at least 500 lines per millimeter.

22. Apparatus as set forth in claim 20, wherein said screen includes a carrier and a layer of zinc phosphor on said carrier.

23. Apparatus as set forth in claim 22, wherein said phosphor consists essentially of zinc silicate of the formula $Zn_2SiO_4$ and trace amounts of manganese.

24. Apparatus as set forth in claim 22, wherein said phosphor consists essentially of particles not greater than 5 $\mu$m.

25. Apparatus as set forth in claim 20, wherein said television camera has a sensitivity of at least 150 microamperes per lumen.

26. Apparatus as set forth in claim 15, wherein said screen consists essentially of a carrier sheet having two major faces and a thickness not greater than 100 $\mu$m, said carrier sheet being substantially transparent to said modified radiation, and a layer of particulate phosphor on one of said major faces, the other major face being directed toward said secondary beam.

27. Apparatus as set forth in claim 26, wherein said carrier sheet consists essentially of a film of polyethylene terephthalate having a thickness not greater than 6 $\mu$m.

28. Apparatus as set forth in claim 26, wherein said phosphor consists essentially of particles of zinc silicate not greater than 5 $\mu$m.

* * * * *